United States Patent
Blumenkranz

(10) Patent No.: US 11,160,618 B2
(45) Date of Patent: *Nov. 2, 2021

(54) FLEXIBLE ELECTROMAGNETIC SENSOR

(71) Applicant: INTUITIVE SURGICAL OPERATIONS, INC., Sunnyvale, CA (US)

(72) Inventor: Stephen J. Blumenkranz, Los Altos Hills, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 158 days.

This patent is subject to a terminal disclaimer.

(21) Appl. No.: 16/694,037

(22) Filed: Nov. 25, 2019

(65) Prior Publication Data
US 2020/0085514 A1 Mar. 19, 2020

Related U.S. Application Data

(63) Continuation of application No. 15/538,829, filed as application No. PCT/US2015/066588 on Dec. 18, 2015, now Pat. No. 10,512,510.

(60) Provisional application No. 62/095,274, filed on Dec. 22, 2014.

(51) Int. Cl.
*A61B 34/20* (2016.01)
(52) U.S. Cl.
CPC ...... *A61B 34/20* (2016.02); *A61B 2034/2051* (2016.02); *A61B 2034/2061* (2016.02)

(58) Field of Classification Search
None
See application file for complete search history.

(56) References Cited

U.S. PATENT DOCUMENTS

| | | |
|---|---|---|
| 5,372,138 A | 12/1994 | Crowley et al. |
| 5,727,553 A | 3/1998 | Saad |
| 6,253,770 B1 | 7/2001 | Acker et al. |
| 6,272,371 B1 | 8/2001 | Shlomo |
| 7,130,700 B2 | 10/2006 | Gardeski et al. |
| 7,197,354 B2 | 3/2007 | Sobe |
| 7,286,868 B2 | 10/2007 | Govari |
| 7,720,322 B2 | 5/2010 | Prisco et al. |
| 10,512,510 B2 | 12/2019 | Blumenkranz |
| 2001/0021831 A1 | 9/2001 | Fleischhacker et al. |
| 2009/0137952 A1 | 5/2009 | Ramamurthy et al. |
| 2010/0331820 A1 | 12/2010 | Prisco et al. |
| 2011/0066029 A1 | 3/2011 | Lyu et al. |
| 2012/0071822 A1* | 3/2012 | Romo ............ A61B 8/12 604/95.04 |

(Continued)

OTHER PUBLICATIONS

International Preliminary Report on Patentability for Application No. PCT/US2015/066588, dated Jul. 6, 2017, 10 pages.

(Continued)

*Primary Examiner* — Douglas X Rodriguez
(74) *Attorney, Agent, or Firm* — Haynes and Boone, LLP

(57) ABSTRACT

A medical instrument may comprise a flexible shaft and a sensing coil extending within the flexible shaft. The sensing coil may include an electrical conductor wound around a flexible core. The flexible core may comprise adjacent flexible pieces of magnetically permeable material that are configured to slide relative to each other in response to a bending of the flexible core.

20 Claims, 5 Drawing Sheets

(56) References Cited

U.S. PATENT DOCUMENTS

2013/0096572 A1    4/2013   Donhowe et al.
2017/0358388 A1    12/2017   Buesseler

OTHER PUBLICATIONS

International Search Report and Written Opinion for Application No. PCT/US2015/066588, dated Apr. 6, 2016, 17 pages.
Seeton, R. M., "Sensitivity of Single Coil Flexible Electromagnetic Sensors for Breathing Measurements," Ottawa-Carleton Institute for Biomedical Engineering, Department of Systems and Computer Engineering, Carleton University, Jan. 9, 2008, pp. 1-27.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FLEXIBLE ELECTROMAGNETIC SENSOR

RELATED APPLICATIONS

This patent application is a continuation of U.S. patent application Ser. No. 15/538,829, filed Jun. 22, 2017, which is the U.S. national phase of International Application No. PCT/US2015/066588, filed Dec. 18, 2015, which designated the U.S. and claims priority to and the benefit of the filing date of U.S. Provisional Patent Application 62/095,274, filed Dec. 22, 2014, the contents of each of which are incorporated herein by reference in their entirety.

BACKGROUND

Electromagnetic sensors provide one way to determine the position and orientation of a portion of a medical instrument during a minimally invasive medical procedure. For example, a minimally invasive lung biopsy procedure may need to navigate a lung catheter through the airways or bronchia of a patient until a distal tip of the lung catheter reaches a target site such as a node in the patient's lungs. The lung catheter may include one or more electromagnetic sensors for measurements of the locations and orientations of lung catheter sections containing the electromagnetic sensors. Typically, each electromagnetic sensor includes one or more sensing coils that act as antennas and generate induced electrical signals when subjected to a magnetic field that varies with time. During a minimally invasive procedure, a field generator can be positioned near the patient to generate a magnetic field having a magnitude or direction or both that varies over time in a controlled manner. Analysis of the electrical signal induced in a single coil may provide measurements of multiple degrees of freedom, e.g., x, y, and z coordinates and pitch and yaw angles, of the coil or the portion of the instrument including the coil.

The strength of the induced signal from a coil in an electromagnetic sensor generally depends on the number of windings in the coil, the area of each winding, and the magnetic permeability of a core running through the windings as well as the magnitude and direction of changes in the magnetic field. For minimally invasive medical instruments, the diameters of the coils need to be small when the diameter of the instrument is small, e.g., to navigate into smaller airways. As a result, the coils in electromagnetic sensors are generally long to allow many windings and generally employ a core made of a material with a high magnetic permeability, e.g., a material with a relative magnetic permeability of about 10 or more. The length and rigidity of a coil in an electromagnetic sensor can limit the flexibility of the instrument in which the electromagnetic sensor is mounted.

SUMMARY

In accordance with an aspect of the invention, an electromagnetic sensor for a minimally invasive medical instrument may bend while measuring the position or orientation of a portion of the medical instrument. In particular, a sensing coil can employ a relatively loose winding of wire or another electrical conductor around a flexible core, and the core can be made flexible through use of high magnetic permeability material that may be in a particulate or powdered form and compounded with a flexible binder, may be stranded as flexible wires, or may be layered as strips of flexible tape. The bend, e.g., a radius of curvature, of the flexible coil can be measured, e.g., using a shape sensor, so that analysis of an induced signal from the flexible coil can account for the sensing coil being bent during a measurement process.

One specific embodiment is a medical system including a sensing coil. The sensing coil includes a flexible core and an electrical conductor. The flexible core contains a magnetically permeable material, and the electrical conductor is wound around the flexible core in a manner that permits use of the sensing coil in a range of configurations from straight to bent with a minimum radius of curvature.

Another specific embodiment is a sensing method. The method generally includes measuring an induced electrical signal in a flexible coil that may be bent. The sensing method may further include measuring a shape of the flexible coil, applying a time-varying magnetic field to the flexible coil, and determining a measurement through analysis of a signal induced in the coil. The analysis of the induced signal may particularly employ a correction factor identified using the shape measured for the flexible coil.

Yet another specific embodiment is a medical instrument including a flexible tube, a first coil, and a second coil. The first and second coil are in a wall of the tube and respectively provide first and second induced signals that depend on a time-varying magnetic field applied to the instrument. The second coil is at a non-zero angle to the first coil, and at least the second coil is bent to fit within the wall of the tube.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

A sensing coil in an electromagnetic (EM) sensor can be flexible enough to bend as a flexible medical instrument containing the EM sensor bends. The coil may be used with an adjacent shape sensor that measures the shape of the coil, e.g., measures a radius of curvature of the coil's centerline axis, and a measurement process analyzing an electrical signal from the coil can use the measured shape in calculations of the degrees of freedom that the EM sensor measures. As a result, a flexible medical instrument can use an EM sensor without limiting the flexibility of the flexible medical instrument.

One particular application of an EM sensor with a flexible sensing coil is during a medical procedure such as a lung biopsy. In particular, a physician or an automated control system navigating a flexible shaft medical device (e.g., a lung catheter) through natural lumens (e.g., lung airways or bronchia) often needs to know of the position and orientation of the distal tip or other portions of the flexible device relative to the patient's tissues. CT scans may provide a three-dimensional map of tissue features such as bronchia, and an EM sensor can sense the position and orientation of a portion of the flexible device in or relative to the tissue features. Such EM sensors may include one or more small flexible sensing coils (e.g., two coils at a non-zero angle to each other), and each coil may act as an antenna in an EM tracking system. In particular, a magnetic field generator may vary electromagnetic fields in a known sequence of orientations such that an induced signal resulting in a straight coil may be sufficient for calculation of the position of the coil in three dimensions (e.g., x, y and z coordinates) and two orientation angles (e.g., angles $e_x$ and $e_y$) about the two axes (e.g., x and y axes assuming the z axis is along the central axis of the coil). Using a second coil at a non-zero angle relative to the first coil can provide another induced signal that is sufficient for calculation of the position and two orientation angles about different axes x' and y'. Accordingly, an EM sensor containing two straight coils may be sufficient for measurement of six degrees of freedom of a section of the flexible instrument containing the coils.

Figure 1A:
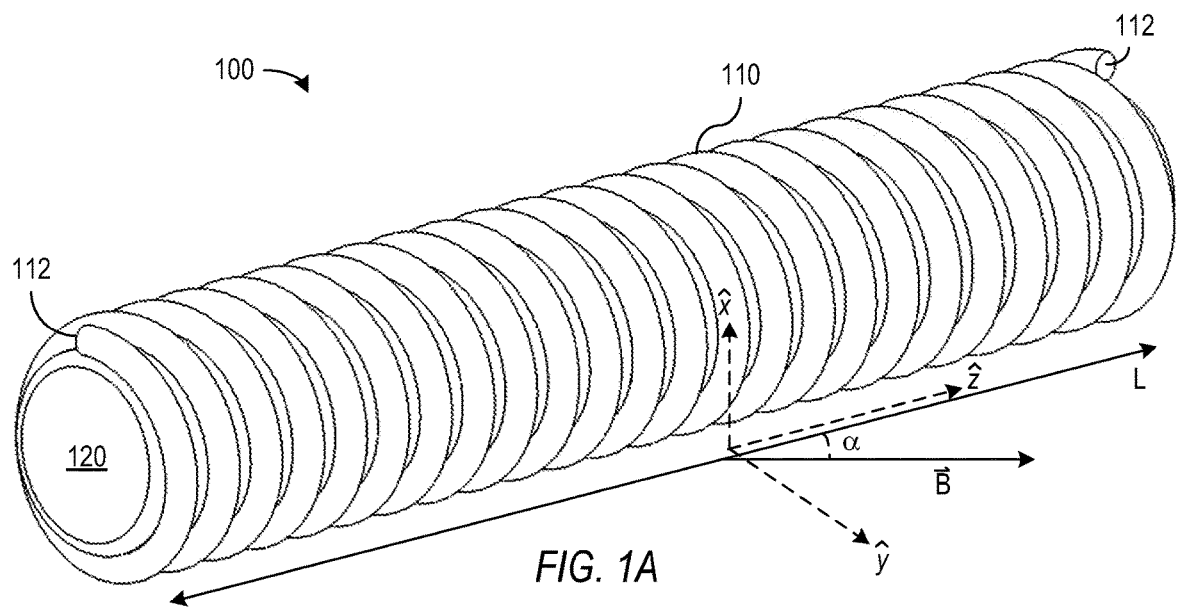
FIGS. 1A and 1B respectively show straight and bent configurations of a flexible coil with a rubberized core containing an elevated magnetic permeability material.
Figure 1B:
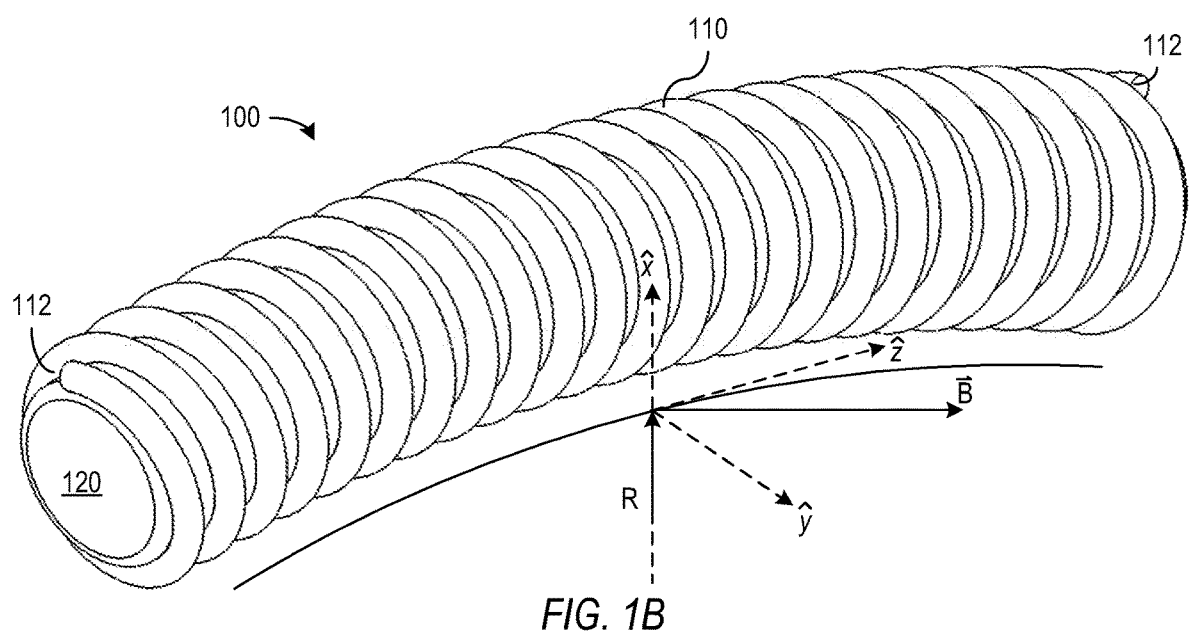

FIGS. 1A and 1B illustrate an example of a flexible sensing coil 100 for use in an EM sensor, particularly in a flexible portion of a medical instrument. Coil 100 is mechanically compliant in bending and may particularly allow coil 100 to be bent about a radius on the order of the overall length L of coil 100 without breakage. For example, coil 100 may be operable in a range of configuration from straight down to a minimum radius of curvature that is twice the overall length of the coil, equal to the overall length of the coil, or even smaller than the overall length of the coil. For an example medical application, coil 100 may be about 10 mm long and about 1 mm in diameter and might be bent to a radius of curvature R of 20, 10, or even 5 mm about a transverse axis, e.g., about an axis parallel to and a distance R below a unit vector ŷ shown in FIG. 1B. In contrast, current miniature EM sensors generally use fine wire wound about a rigid core such as Mn—Zn ferrite ceramic that resists bending in response to forces typically available in a medical device, and current EM sensing coils break if significantly bent.

Coil 100 of FIGS. 1A and 1B includes a conductor 110 that is wound around a flexible magnetic core 120. Conductor 110 may be a conductive wire such as a copper wire with an insulating coating. Conductor 110 may be wound loosely, e.g., with a pitch that may be greater than the thickness of conductor 110, in order to facilitate bending coil 100 without causing damaging stress to conductor 110 or core 120. In an EM sensor, conductor 110 may include a number of winds selected according to the applied electromagnetic field and the desired induced signal strength, and conductor 110 may have ends 112 connected to conductive leads. Coil 110 also may be wound in multiple layers, and ends 112 may both be at the same end of coil 100 to facilitate connection of lead wires. As described further below, leads extending from ends 112 of conductor 110 may connect to sensing logic that analyzes an induced electrical signal $V_{INDUCED}$ generated in coil 100 when a magnetic field $\vec{B}$ that varies in time extends through coil 100. FIGS. 1A and 1B show unit vectors x̂, ŷ, and ẑ for a rectangular co-ordinate system in which the z or ẑ axis is along the average length direction of coil 100 and the y or ŷ axis is perpendicular to the circular arc which best approximates the curve of coil 100 when bent as shown in FIG. 1B. In general, magnetic field $\vec{B}$ may be at any angles to unit vectors x̂, ŷ, and ẑ.

Magnetic core 120 of coil 100 is flexible and has an elevated magnetic permeability, so that core 120 serves to concentrate surrounding magnetic flux inside coil 100 and thus increase the inductance of coil 100 and the sensitivity of an EM sensor including coil 100. Core 120 may be a solid cylinder in the unbent configuration and may include one of a variety of elastically or plastically deformable materials containing particles with high or elevated magnetic permeability. Suitable deformable materials for core 120 include a rubber compounded Mn—Zn ferrite or Moly-Permalloy or Sendust powder. Other deformable magnetically permeable materials also may be used.

Figure 2A:
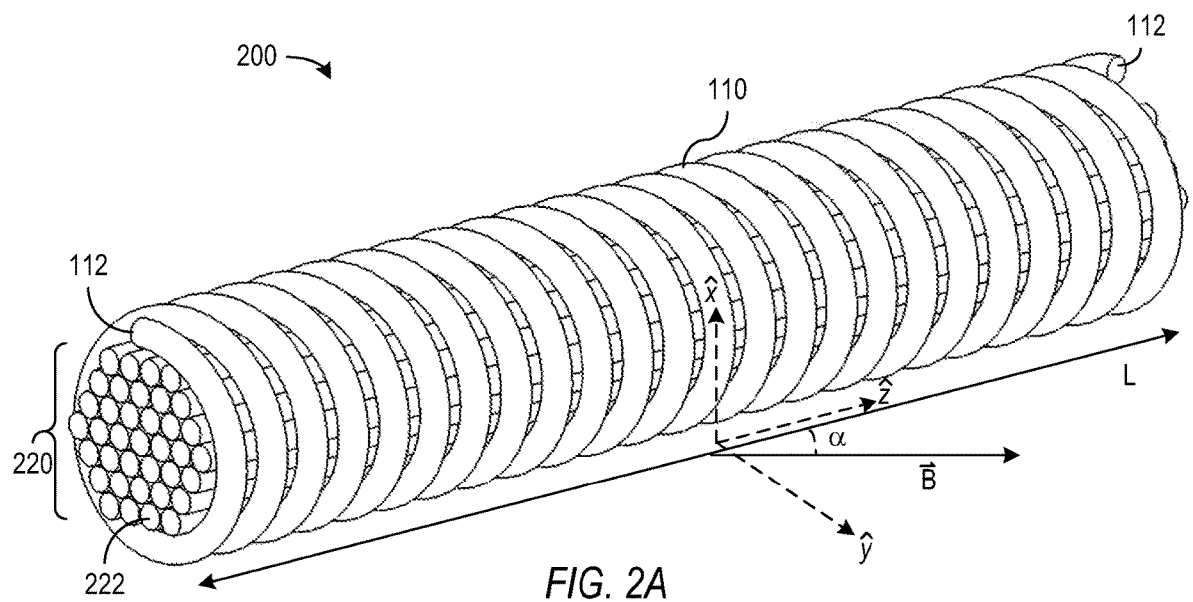
FIGS. 2A and 2B respectively show straight and bent configurations of a flexible coil with a core containing stranded material with elevated magnetic permeability.
Figure 2B:
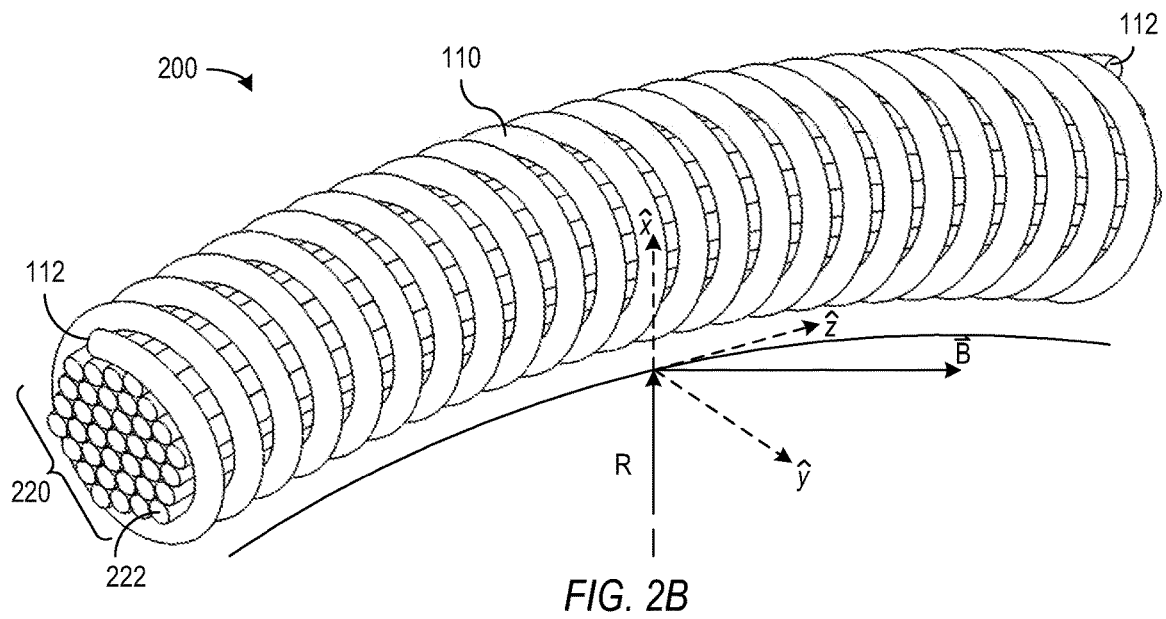

Alternatively, a core for a flexible coil may include multiple flexible strands. FIGS. 2A and 2B, for example, illustrate a flexible sensing coil 200 respectively in unbent and bent configurations. Coil 200 includes an electrical conductor 110 such as described above, but conductor 110 in coil 200 is wound around a core 220 made up of multiple strands 222 of material with an elevated magnetic permeability, i.e., a magnetic permeability greater than 1. Strands 222 may have a high magnetic permeability, i.e., a magnetic permeability greater than 10. (As used herein, "magnetic permeability" refers to a relative permeability, where the permeability of vacuum is 1.) Each strand 222 may, for example, be a permalloy metal wire of sufficiently small diameter to readily deform in response to forces available in robotic medical instruments and to deform repeatedly for the required bending cycle life at the expected minimum for bend radius R of coil 200. Strands 222 may further slide relative to each other as needed to accommodate bending of sensing coil 200.

Figure 3A:
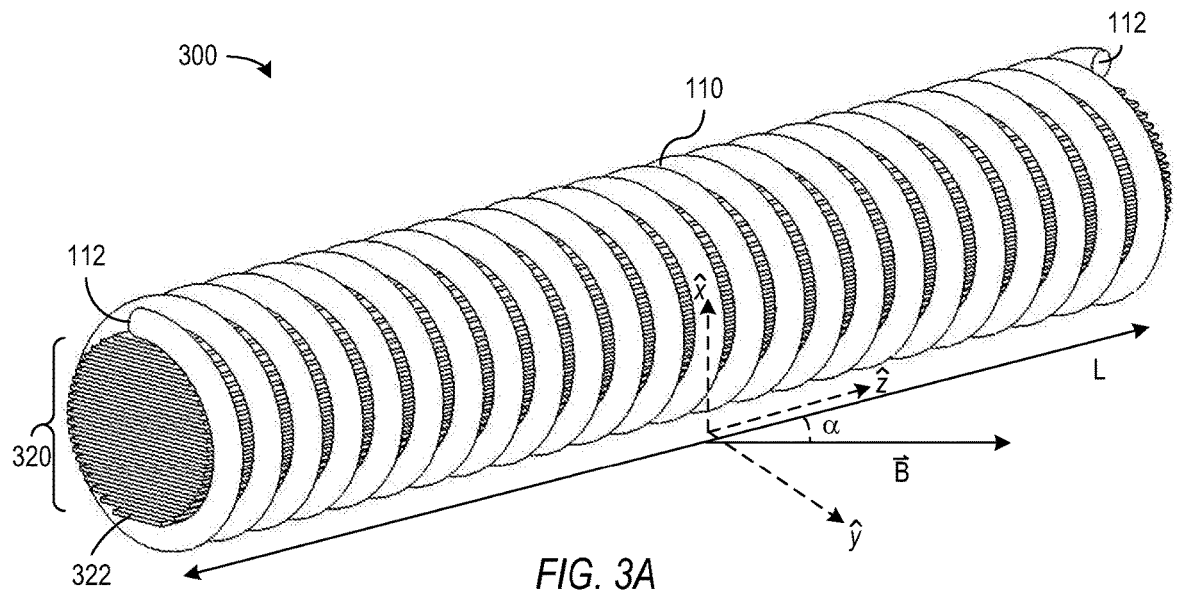
FIGS. 3A and 3B respectively show straight and bent configurations of a flexible coil with a core containing flexible layers of material with elevated magnetic permeability.
Figure 3B:
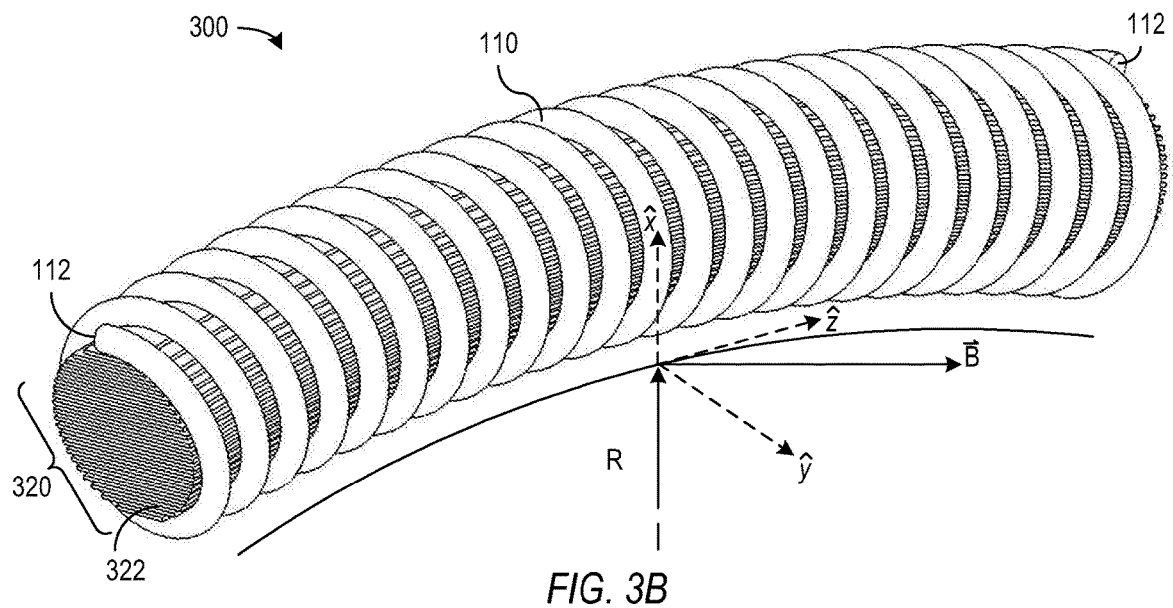

In another alternative configuration, a core for a flexible coil may include multiple layers or pieces of flexible tape. FIGS. 3A and 3B, for example, illustrate a flexible sensing coil 300 respectively in unbent and bent configurations. Coil 300 includes an electrical conductor 110 such as described above, but conductor 110 in coil 300 is wound around a core 320 made up of multiple tapes 322 of material with a high magnetic permeability. Tapes 322 have an elevated magnetic permeability, i.e., a magnetic permeability greater than 1, or a high magnetic permeability, i.e., a magnetic permeability greater than 10. Each tape 322 may, for example, be a permalloy metal tape of sufficiently small thickness to readily deform (at least in one direction) in response to forces available in robotic medical instruments and to deform repeatedly for the required bending cycle life at the expected minimum of bend radius R of coil 300. During such bending, individual tapes 322 may slide relative to other tapes 322. The flexibility of the tape-based core 320, may differ from the flexibility of core 220 of FIG. 2, in tape-based core 320 of FIG. 3 may be flexible for bending only in a plane perpendicular to tapes 322 and rigid to resist bending in other directions. Accordingly, coil 300 may be adapted to uses where only one plane of bending is necessary or desired.

Cores 120, 220, and 320 can employ a variety of known materials to achieve either elevated or high magnetic permeability. For example, high magnetic permeability metals with magnetic permeability on the order of 10,000 or more are commercially available with trade names such as Co- Netic, Mu metal, Moly-Permalloy, High Perm 49, Permalloy, Supermalloy, Super Mumetal, Nilomag, Sanbold, HyMu 80, and HyMu 800. High magnetic permeability ferrites such as Mn—Zn are commercially available by grade such as H-grade, W-grade, and F-grade corresponding to magnetic permeability of 15,000, 10,000, and 5,000, respectively. High magnetic permeability nanocrystalline material such as VitroPerm 500F and metal powders such as MPP (moly-permalloy powder), HiFlux, and Sendust are also commercially available. Such materials may generally be used in one or more of the example implementations illustrated in FIGS. 1A, 1B, 2A, 2B, 3A, and 3B.

Figure 4:
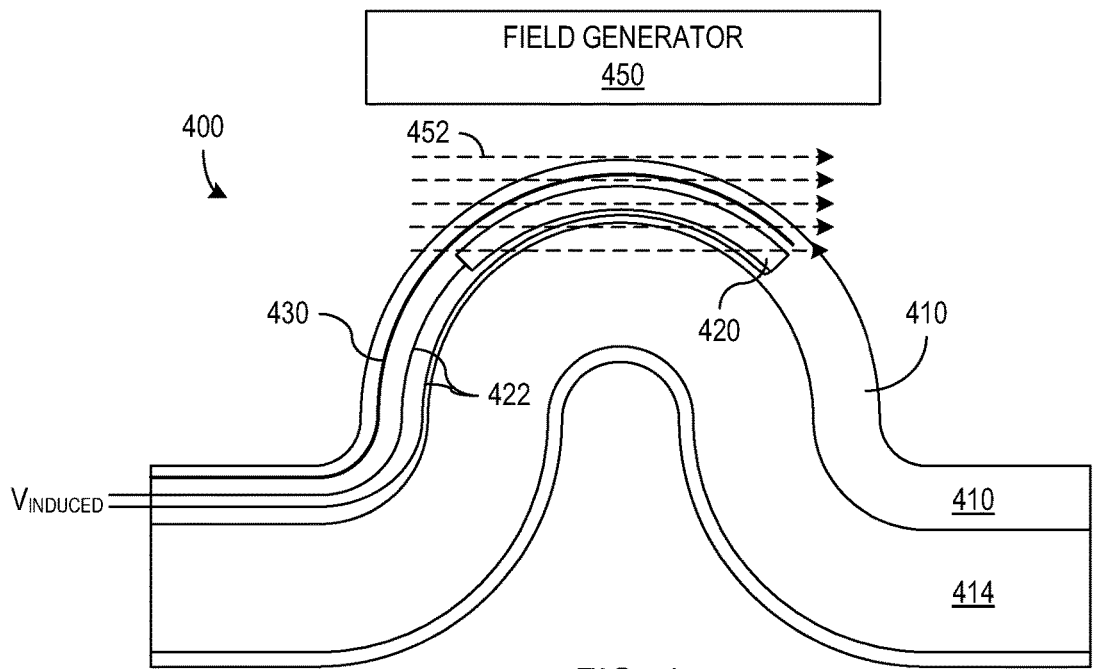
FIG. 4 shows a portion of a flexible instrument including a flexible electromagnetic sensor.

In a medical system, a flexible coil such as coil 100, 200 or 300 may be mounted in a flexible portion of a medical instrument. FIG. 4 shows a cross-section along a length axis of a flexible section 400 of a medical instrument such as a lung catheter. In the illustrated implementation, flexible section 400 includes a flexible wall 410 surrounding a lumen 414 that may, for example, be sized to accommodate a tool (not shown) that may be inserted through lumen 414. A flexible coil 420, which may be identical to coil 100, 200 or 300, may be embedded in or otherwise mounted on wall 410 and bends as flexible section 400 bends. As a result, the shape, orientation, and direction of flexible coil 420 depends on the shape, orientation, and direction of flexible section 400 at the location in which flexible coil 420 is mounted or embedded. Since coil 420 is able to bend in this manner, the part of wall 410 containing coil 420 does not need to remain straight and does not need to otherwise accommodate coil rigidity. Accordingly, flexible section 400 may be able to tightly bend. A shape sensor 430, which may be a fiber optic shape sensor, runs along flexible section 400 including flexible coil 420, so that the shape of section 400 and the shape of coil 420 can be measured. The shape of coil 420 may be used as described below in a process of determining measured degrees of freedom from an induced voltage signal $V_{INDUCED}$ that coil 420 generates on leads 422. In general, a changing magnetic field 452 from a field generator 450 induces a voltage signal $V_{INDUCED}$ in coil 420 that is proportional to the time derivative of the magnetic flux through the windings of coil 420, and the magnetic flux through each winding is equal to the product of the area of the winding and the magnitude of the magnetic field component normal to the area of the winding. Since coil 420 is bent, the windings of coil 420 may have different normal directions and may provide different contributions to the induced electrical signal $V_{INDUCED}$. However, the high magnetic permeability of the core of coil 420 may tend to shape the magnetic field so that the effect of the bend in coil 420 is reduced. In one specific embodiment of system 400 of FIG. 4, the variation of sensor output $V_{INDUCED}$ with respect to bend radius R and the apparent pointing direction of coil 420 when in a bent configuration are calibrated (e.g., in a fixture adapted for that purpose).

The change in inductive response may be illustrated by considering the example of FIGS. 1A and 1B again. FIG. 1A particularly shows sensing coil 100 in its straight or unbent configuration. Applying a time varying magnetic field $\vec{B}$ that is approximately uniform in the vicinity of coil 100 induces a voltage $V_{INDUCED}$ as given in Equation 1 when the coil 100 is in the straight configuration of FIG. 1A. In Equation 1, $\alpha$ is the angle between the magnetic field $\vec{B}$ and the length axis of the coil, N is the number of windings in the coil, A is the area of each winding, and k depends on the magnetic permeability of the core of the coil.

$$V_{INDUCED} = -kNA\frac{d|B|\cos\alpha}{dt} \qquad \text{Equation 1}$$

FIG. 1B shows coil 100 when coil 100 is bent. Such bending may result from a transverse force or bending moment on coil 100 if coil 100 has a relaxed state that is straight as shown in FIG. 1A. A transverse force or bending moment may result from actuation or bending of a flexible portion 400 of an instrument in which coil 100 is embedded. In the example of FIG. 1B, the bend provides coil 100 with an average radius of curvature R about an axis parallel to and offset by distance R from axis ŷ. Radius of curvature R may have any value with greater than the tightest or minimum radius of curvature R that coil 100 is designed to tolerate and may be the same order of magnitude as, equal to, or less than a length L of coil 100. (More generally, a flexible coil may have a compound bend in which portions of the coil are bent about different axes and with different radii of curvature, but in a system in which the length of a coil is on the order or smaller than the tightest expected radius of curvature, compound bending may be limited or well approximated by a circular arc.) Bending of coil 100 may change the inductive response of coil 100 to a time-varying magnetic field $\vec{B}$. In particular, applying a time varying magnetic field $\vec{B}$ that spatially is approximately uniform in the vicinity of coil 100 induces a voltage $V_{INDUCED}$ as given in Equation 2 when the sensing coil is in the bent configuration of FIG. 1B. In Equation 2, N is the number of windings in the coil, A is the area of each winding, R is the average radius of curvature of the coil, k depends on the magnetic permeability of the core of the coil, and f(R) is a correction function dependent on bend radius R or more generally dependent on the geometry and orientation of the coil relative to applied magnetic field $\vec{B}$. Angle $\alpha$ is the angle between applied magnetic field $\vec{B}$ and unit vector along the average pointing direction ẑ of the coil. (Equation 2 assumes that the shape of coil 100 may be sufficiently approximated as a circular arc with an average radius R and in an x-z plane, which has a normal vector ŷ.) The change in response of coil 100 represented by correction factor f(R) may be close to one or predictable so that a measurement process can ignore or compensate for variations in the electrical output from coil 100, depending on the desired measurement accuracy.

$$V_{INDUCED} = -kNA\frac{d|B|\cos\alpha}{dt}f(R) \qquad \text{Equation 2}$$

Correction factor f(R) more generally may depend on the direction of magnetic field $\vec{B}$ relative to the average pointing direction ẑ and the normal vector ŷ to the x-z bending plane. Correction factor f(R) may also depend on the magnetic permeability k of the core and the degree to which the presence of the high permeability core dominates over the geometric effect of the curved shape of the coil. In some application, these effects may be ignored, and a coil may be calibrated by measuring the effect of bending curvature R in a laboratory setting, constructing a look-up table or other model of correction factor f(R), and then using the curvature measured by the fiber optic shape sensor to apply correction factor f(R) to induced voltage $V_{INDUCED}$ in analysis that determines measurements of the position and orientation of an EM sensor employing the coil.

Equations 1 and 2 and the description above were provided with reference to coil 100 of FIGS. 1A and 1B. Equations 1 and 2 and the description are, however, equally applicable to coil 200 of FIGS. 2A and 2B and to coil 300 of FIGS. 3A and 3B. More generally, any flexible coil used in an EM sensor may be expected to produce an induced voltage $V_{INDUCED}$ that depends on the present shape and particularly on the radius of curvature of the coil.

Figure 5:
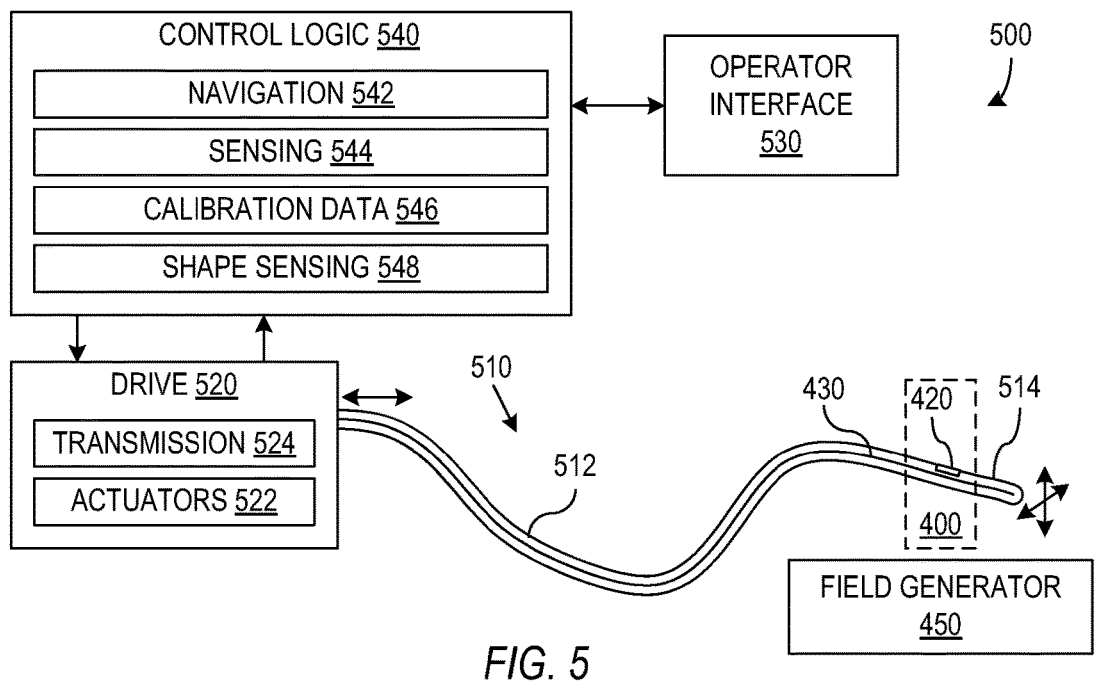
FIG. 5 is a block diagram of a medical system employing sensing coils that are flexible and operable while bent.

The induced voltages from one or more sensing coils may be analyzed in a larger system to determine measurements for multiple degrees of freedom of motion for the coils. FIG. 5 schematically illustrates one specific implementation of a medical system 500 in accordance with one embodiment of the invention employing EM sensing with flexible sensing coils. In the illustrated embodiment, system 500 includes a lung catheter 510, a steering drive mechanism 520, an operator interface 530, and control logic 540.

Catheter 510 is a flexible device having one or more lumens including a tool lumen that can accommodate interchangeable probes such as a biopsy needle or a camera probe. The construction of catheter 510 can be of any type that provides catheter 510 with suitable length, diameter, flexibility, and acceptable friction surface. In the illustrated configuration, catheter 510 has a proximal section 512 that is flexible and a distal section 514 that is steerable. During a medical procedure, a portion of proximal section 512 and all of distal section 514 may be inserted along a natural lumen such as an airway of a patient. Sections 512 and 514 may have the same or different diameters.

Catheter 510, as noted above, includes at least one tool lumen for interchangeable probe systems and may further include smaller lumens for pull wires, sensor lines, illumination fibers, or permanent vision systems or for introduction or removal of fluids or medication to or from a work site. In the illustrated implementation, distal section 514 may have a mechanical structure (not shown) that may be actuated through tendons or pull wires (not shown) that extend from a steering drive mechanism 520 through proximal section 512 to distal section 514 of catheter 510. Alternatively or additionally, mechanical elements anywhere along the length of catheter 510 may be similarly articulated using drive tendons or other mechanisms.

Steerable section 514 in the illustrated configuration is remotely controllable and particularly has a pitch and a yaw that can be controlled using actuating tendons. All or a portion of section 514 may be more flexible than the remainder of catheter 510 to assist in isolating actuated bending to section 514 when steering drive mechanism 520 pulls on actuating tendons. However, the entirety of catheter 510 should have sufficient compliance and a sufficiently small minimum radius of curvature to follow or conform to the shape of a natural lumen, e.g., an airway.

Steering drive mechanism 520 of FIG. 5, which pulls on tendons to actuate catheter 510, includes a mechanical system or transmission 524 that converts the movement of actuators 522, e.g., electric motors, into tensions in or movements of the tendons that run through and connect to portions of catheter 510. The movement and pose of catheter 510 or at least a portion of distal section 514 can thus be controlled through computer assisted selection or generation of respective actuation signals for actuators 522 in steering drive mechanism 520. In addition to actuation elements of catheter 510, steering drive mechanism 520 may be used to control other movement of catheter 510 such as rotation or roll of the proximal end of catheter 510, which may also be powered through actuators 522 and transmission 524. Back-end mechanisms or transmissions that are known for flexible-shaft instruments could in general be used or modified for steering drive mechanism 520. For example, some known drive systems for flexible instruments are described in U.S. Pat. App. Pub. No. 2010/0331820, entitled "Compliant Surgical Device," which is hereby incorporated by reference in its entirety.

Control logic 540 controls actuators 522 in steering drive mechanism 520 to selectively pull on the tendons as needed to actuate catheter 510 and control the pitch and yaw of the distal tip 514 of catheter 510 and controls actuators 522 to control rotation and to control movement of catheter 510 in an insertion direction. In general, control logic 540 operates in response to commands from a user, e.g., a surgeon, physician, or other human user using operator interface 530, and the user may operate interface 530 in response to a view that a vision system provides or measurements from a sensor system including magnetic field generator 450 and flexible sensing coil 420. Control logic 540 employs sensor signals, e.g., induced signal $V_{INDUCED}$ from coil 420, in measuring degrees of freedom, e.g., position co-ordinates and pitch, yaw, and roll angles, for a portion of catheter 510 containing coil 420. Control logic 540 may be implemented using a general purpose computer with suitable software or firmware and/or using device-specific hardware to interpret signals from operator interface 530 to generate actuation signals for actuators 522 and interpret signals from coil 420 and magnetic field generator 450 to measure degrees of freedom of flexible section 400.

In the illustrated embodiment, control logic 540 includes multiple modules 542, 544, and 548 that implement different processes or modes for use of catheter 510. As used herein, the term "module" refers to a combination of hardware a processor such as an integrated circuit or other circuitry) and software (e.g., machine or processor-executable instructions, commands, or code such as firmware, programming, or object code). A combination of hardware and software includes hardware only (i.e., a hardware element with no software elements), software hosted at hardware (e.g., software that is stored at a memory and executed or interpreted or at a processor), or hardware and software hosted at hardware.

Navigation module 542 may operate while a user steers catheter 510 to a target location or configuration. Navigation module 542 may interpret or convert control signals from operator interface 530 and may generate actuation signals for actuators 522. Operator interface 530 may include standard input/output hardware such as a vision system, a display, sensor readouts, a keyboard, a joystick, a foot pedal, a pointing device such as a mouse, or similar I/O hardware that may be customized or optimized for a surgical environment. In general, operator interface 530 provides information to the user and receives instructions from the user. For example, operator interface 530 may provide the user with data including images and measurements made in system 500.

Flexible section 400 includes an EM sensor containing one or more flexible sensing coils 420 that act as antennas and respectively generate induced signals $V_{INDUCED}$ when field generator 450 generates a magnetic field that varies over time. Additionally, a shape sensor 430 may be employed to measure the shape of a portion of catheter 510 at least including any flexible coils 420 that may be bent when catheter 510 bends. In the implementation of FIG. 5, shape sensor 430 is a fiber optic shape sensor and may extend along the entire length or a distal portion of catheter 510, so that shape measurement module 548 can use measurements of the interference of light transmitted on optical fiber and determine the shape of at least a portion of catheter 510. Such shape sensors using fiber gratings are further described in U.S. Pat. No. 7,720,322, entitled "Fiber Optic Shape Sensor," which is hereby incorporated by reference in its entirety. Instead of a shape sensor, other implementations could use other systems for sensing the shape of the flexible coils or other portions of catheter 510.

Figure 6:
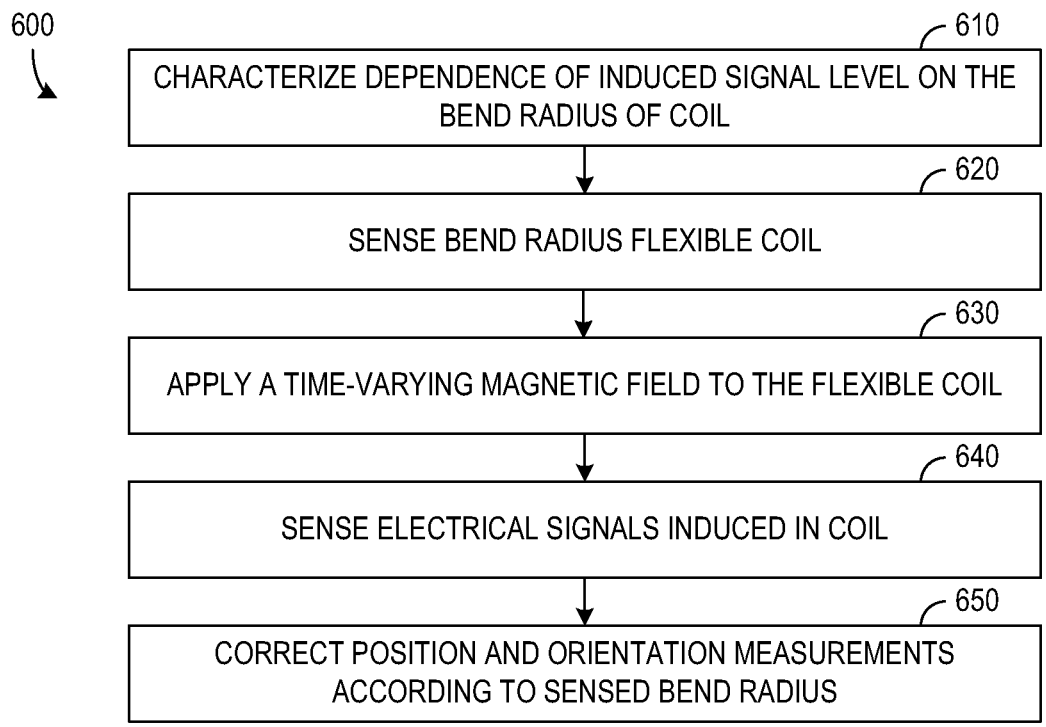
FIG. 6 is a flow diagram of a process for adjusting measurements to compensate for bending of a flexible sensing coil.

Sensing module 544 receives or has access to an induced voltage signal $V_{INDUCED}$ from each flexible coil 420, shape measurements determined from shape sensor 430, and control data indicating the parameters of the magnetic field from magnetic field generator 450. Sensing module 540 can use such information to determine degree of freedom measurements. For example, a process 600 of FIG. 6 is an example of one method for determining degree of freedom measurements. Process 600 includes a process block 610 that characterizes how an induced signal $V_{INDUCED}$ from a flexible coil depends on the radius of curvature of the coil. Some implementations further characterize the dependence of induced signal $V_{INDUCED}$ on the orientation of the curved coil relative to an applied magnetic field. Calibration data that characterizes a flexible coil can be determined from the design of the coil or measured before or during manufacture of the coil or a system using the coil. One way to characterize a sensing coil may be to determine the functional dependence of a correction factor f(R) described with reference to Equation 2 above. The correction factor f(R) functionally depends on the present radius of curvature R of the coil. For example, sensing module 544 of FIG. 5 may employ calibration data 546 that characterizes correction factor f(R) and is stored in memory accessible to control logic 540. In one implementation, calibration data 546 may include a look-up table that provides values of correction factor f(R) indexed by radius R. Optionally, interpolation techniques may be employed if necessary to achieve a desired accuracy for correction factor f(R). Alternatively, correction factor f(R) could be calculated using a formula or other techniques. Characterization block 610 may be performed once and does not need to be repeated for every determination of measured degrees of freedom.

A process block 620 determines the present bend radius of a flexible coil for which degrees of freedom are to be measured. In the system 500 of FIG. 5, shape sensor 430 may be a fiber optic shape sensor that extends through flexible portion 420 and beyond, e.g., to the distal tip of catheter 510. The shape of flexible coil 420 may thus correspond to only a portion of the shape measured using shape sensor 430. In one implementation, the measured shape data indicates an average radius of curvature R of flexible coil 420. EM sensing may be more accurate than measurements using a shape sensor such as a fiber optic shape sensor because errors in shape determination may propagate and become larger as distance from a known reference point increases. Further, measurements determined using sensing coil 420 can provide a reference point for improved accuracy in determining the shape of catheter 510 using a shape sensor.

A block 630 represents applying a time-varying magnetic field to the instrument and particularly the sensing coil. The time varying magnetic field may be applied using a variety of techniques including known EM sensing scenarios. One specific EM sensing scenario keeps a direction of an applied magnetic field $\vec{B}$ constant for a time interval, while the magnitude of the applied magnetic field $\vec{B}$ oscillates. With this scenario, the direction of the applied magnetic field $\vec{B}$ may be switched systematically through a series of directions respectively corresponding to a series of time intervals. The correction factor f(R) generally remains approximately constant during short sensing intervals, even if the shape of the instrument and sensing coil may change over a more extended time. An alternative EM sensing scenario superimposes magnetic fields that have different directions and that oscillate with different frequencies, and a resulting induced signal $V_{INDUCED}$ in a sensing coil may thus include separable frequency components that correspond to different magnetic field directions.

A process block 640 senses induced electrical signal $V_{INDUCED}$ and separates (time or frequency multiplexed) components that correspond to different magnetic field directions. The magnitudes of the different components may be related by multiple simultaneous equations that depend on the position and orientation of the coil relative to the magnetic field generator and on the measured radius of curvature of the coil. A process block 650 identifies and solves the simultaneous equations, which may include correction factors f(R), to determine measurements of the degrees of freedom of an EM sensor containing a flexible sensing coil. For example, correction factors f(R) based on measurements of R determined through shape sensing can be used in the equations that EM sensing employs to determine measurements of multiple degrees of freedom of the coil. In another example, the curvature of the flexible coil may have a negligible effect, so that position and orientation measurements of a desired accuracy may be found using conventional EM sensor analysis without needing to employ any correction factors. Other EM sensing scenarios may employ other techniques for constructing simultaneous equations or otherwise solving for measurements of degrees of freedom.

Conventional EM sensors that measure six degrees of freedom generally require two straight coils. This can be easily understood considering a straight coil such as coil 100 in the unbent configuration of FIG. 1A. Coil 100 in the unbent configuration is symmetric about a length axis, so a roll angle about that axis does not change the magnetic flux through the coil 100. Accordingly, EM sensing using just coil 100 in the unbent configuration cannot distinguish the roll angle, and only five degrees of freedom of coil 100 can be measured using standard EM sensing techniques. A second straight coil at a non-zero angle to the first sensing coil would be unable to distinguish an angle about a different symmetry axis, but the combination of the two straight coils can together provide measurements of six degrees of freedom. In contrast, a bent coil such as coil 100 in the bent configuration of FIG. 1B does not have the same symmetry as a straight coil.

Figure 7:
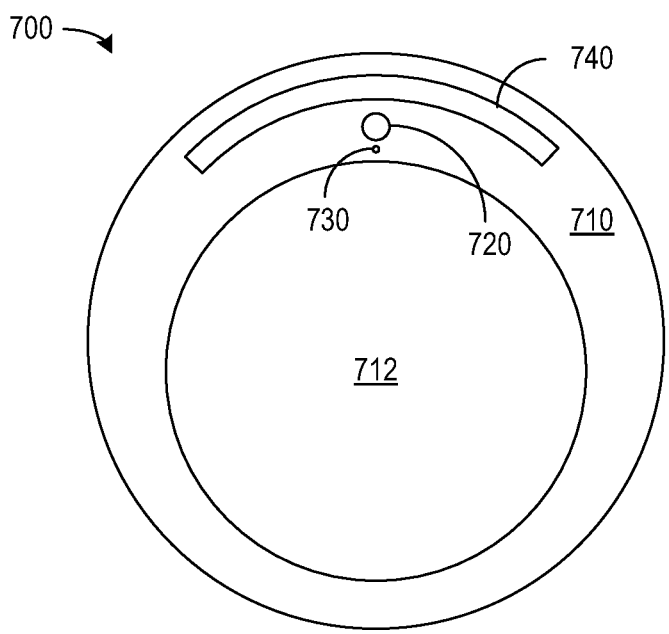
FIG. 7 shows a cross-section of a shaft of a medical instrument including a pair of sensing coils, one of which is bent to fit within the walls of the shaft.

Another advantage of EM sensing coils that may be bent is that such coils may be easier to accommodate in small instruments. FIG. 7, for example, shows a cross-section of a medical instrument 700 such as a lung catheter. Instrument 700 has a shaft 710 with one or more lumens 712. Lumen 712 may be sized to accommodate a surgical tool such as a biopsy needle, but for applications such as a lung catheter, the diameter of shaft 710 may be only a few millimeters to permit insertion into small bronchia. A flexible coil 720 and a shape sensor 730, which may be substantially identical to coil 420 and shape sensor 430 described above and illustrated in FIG. 4, may be directed along the length of shaft 710. An EM sensor may further use a second coil 740 at a non-zero angle relative to coil 720 for measurement of six degrees of freedom. In general, coil 740 may be positioned at a right angle to coil 720 for measurement accuracy. As shown in FIG. 7, coil 740 may be bent according to the curvature of wall 710. A perpendicular arrangement of coils 720 and 740 may be desirable because the equations that need to be solved to determine six degrees of freedom using two sensing coils at a small skew angle are generally ill-conditioned and may give a less accurate result. Two coils at right angles may be the most mathematically desirable configuration, but a configuration in which coil 740 is not perpendicular to coil 720 and is shaped like a portion of a corkscrew or helix may accommodate a greater length for coil 740. In contrast to bent coil 740, a straight coil at a non-zero angle to coil 720 may be more difficult to fit within the boundaries of walls 710. Coil 740 may be a flexible coil to bend as needed or could be a rigid coil with a permanently curved shape.

Some implementations of elements described herein can be implemented in a computer-readable media, e.g., a non-transient media, such as an optical or magnetic disk, a memory card, or other solid state storage containing instructions that a computing device can execute to perform specific processes that are described herein. Such media may further be or be contained in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:

1. A medical instrument comprising:
   a flexible shaft; and
   a sensing coil extending within the flexible shaft, the sensing coil including an electrical conductor wound around a flexible core, wherein the flexible core comprises adjacent flexible pieces of magnetically permeable material that are configured to slide relative to each other in response to a bending of the flexible core.

2. The medical instrument of claim 1, wherein the flexible shaft includes a flexible wall surrounding a lumen and wherein the sensing coil is arranged within the flexible wall.

3. The medical instrument of claim 2, wherein the sensing coil extends parallel to a longitudinal axis of the flexible shaft.

4. The medical instrument of claim 2, wherein the sensing coil is arranged within the flexible wall in a curve around a longitudinal axis of the flexible shaft.

5. The medical instrument of claim 2, wherein the sensing coil is arranged in a helical shape within the flexible wall.

6. The medical instrument of claim 1, further comprising:
   a steering drive mechanism, wherein the flexible shaft includes a steerable section configured for actuation by the steering drive mechanism.

7. The medical instrument of claim 1, wherein an actuatable mechanical structure is disposed at a distal portion of the flexible shaft.

8. The medical instrument of claim 1, further comprising:
   an optical fiber shape sensor extending within the flexible shaft.

9. The medical instrument claim 8, further comprising:
   a sensing module configured to receive a signal from the sensing coil and a bend measurement from the optical fiber shape sensor to determine a direction of a portion of the flexible shaft containing the sensing coil.

10. The medical instrument of claim 1, wherein the flexible pieces of magnetically permeable material include a plurality of tapes, wherein each tape of the plurality of tapes has a magnetic permeability greater than 1.

11. The medical instrument of claim 1, wherein the sensing coil is as flexible as the flexible shaft.

12. A medical system comprising:
    a flexible shaft;
    a sensing coil extending within the flexible shaft, the sensing coil including an electrical conductor wound around a flexible core, wherein the flexible core comprises adjacent flexible pieces of magnetically permeable material that are configured to slide relative to each other in response to a bending of the flexible core; and
    a processor configured to receive a first sensing signal from the sensing coil.

13. The medical system of claim 12, further comprising:
    a magnetic field generator, wherein the processor is further configured to receive a second sensing signal from the magnetic field generator.

14. The medical system of claim 12, further comprising:
    an actuator configured to steer a portion of the flexible shaft, wherein the processor is further configured to provide actuation signals to the actuator.

15. The medical system of claim 12, further comprising:
    an optical fiber shape sensor extending within the flexible shaft, wherein the processor is further configured to determine a shape of the flexible shaft based on a second sensing signal received from the optical fiber shape sensor.

16. The medical system of claim 15, wherein the processor is further configured to determine the shape of the flexible shaft based on the first sensing signal and the second sensing signal.

17. The medical system of claim 15, wherein the processor is further configured to calibrate the sensing coil by using the second sensing signal to reference calibration data.

18. The medical system of claim 12, wherein the processor is further configured to determine, based on the first sensing signal, a position of a portion of the flexible shaft.

19. The medical system of claim 12, wherein the processor is further configured to determine, based on the first sensing signal, an orientation of a portion of the flexible shaft.

20. The medical system of claim 12, wherein the processor is further configured to:
    receive control signals from an operator interface; and
    responsive to the control signals, generate an actuation signal for steering a portion of the flexible shaft.

* * * * *